(12) United States Patent
Burstein

(10) Patent No.: US 6,503,439 B1
(45) Date of Patent: Jan. 7, 2003

(54) PROCESS FOR FORMING SHAPED ARTICLES OF ULTRA HIGH MOLECULAR WEIGHT POLYETHYLENE SUITABLE FOR USE AS A PROSTHETIC DEVICE OR A COMPONENT THEREOF

(76) Inventor: Albert H. Burstein, 363 Mourning Dove Dr., Sarasota, FL (US) 34236

( * ) Notice: Subject to any disclaimer, the term of this patent is extended or adjusted under 35 U.S.C. 154(b) by 130 days.

(21) Appl. No.: 09/594,275

(22) Filed: Jun. 15, 2000

(51) Int. Cl.⁷ .............................................. B29C 35/08
(52) U.S. Cl. ......................... 264/469; 264/83; 264/322; 264/323; 264/331.17; 264/473; 264/483; 264/488; 264/494; 422/22; 422/34; 522/161
(58) Field of Search .......................... 264/83, 322, 323, 264/331.17, 469, 473, 483, 488, 494; 522/161; 422/22, 34

(56) References Cited

U.S. PATENT DOCUMENTS

| | | | |
|---|---|---|---|
| 5,030,402 A | 7/1991 | Zachariades | 264/322 |
| 5,721,334 A | 2/1998 | Burstein et al. | 526/352 |
| 6,017,975 A | 1/2000 | Saum et al. | 522/161 |
| 6,228,900 B1 * | 5/2001 | Shen et al. | 522/153 |

FOREIGN PATENT DOCUMENTS

| | | |
|---|---|---|
| EP | 0 729 981 A1 | 4/1996 |
| EP | 0 722 973 A1 | 7/1996 |
| EP | 0923945 A2 * | 6/1999 |

OTHER PUBLICATIONS

Journal of Bone and Joint Surgery vol. 76–A No. 7 Jul. 1994 pp 1052–1055.
Journal of bone and Joint Surgery vol. 76–A No. 7 Jul. 1994 pp 1080–1090.
Abstract of JP 04198201 (Jul. 17, 1992).

* cited by examiner

Primary Examiner—Leo B. Tentoni
(74) Attorney, Agent, or Firm—Richard J. Dankyo, Esq.; Michael A. Nicodema, Esq.; Dreier & Baritz LLP

(57) ABSTRACT

Disclosed is a method of producing a shaped article suitable for use as the load bearing component of a prosthetic device formed from ultrahigh molecular weight polyethylene. polyethylene.

26 Claims, No Drawings

PROCESS FOR FORMING SHAPED ARTICLES OF ULTRA HIGH MOLECULAR WEIGHT POLYETHYLENE SUITABLE FOR USE AS A PROSTHETIC DEVICE OR A COMPONENT THEREOF

BACKGROUND OF INVENTION

1. Field of Invention

This invention relates to a process for forming shaped articles, which can be used as prosthetic devices, which are formed of cross-linked ultrahigh molecular weight polyethylene ("UHMWPE"). The articles exhibit an improved combination of wear resistance and mechanical properties, rendering them useful as the load bearing component in prosthetic knee joints, prosthetic hip joints and as bearing components for other prosthetic replacement joints for the human body. In particular, the shaped articles formed according to the process are suited for use as the lining of an acetabular cup of a prosthetic hip joint.

2. Description of Related Art

UHMWPE, which possesses an average molecular weight of between about 1 million and about 10 million, is used to make prosthetic devices, such as the ones enumerated above. UHMWPE can be formed into the devices by techniques that include: (1) direct compression molding UHMWPE resin into the final shape of the device; (2) ram extrusion of a UHMWPE powder into cylindrical bar stock that is several inches in diameter, and machining the implant from the bar stock and (3) molding large sheets of UHMWPE and machining the implant from the molded sheet. The molded sheets can be up to 8 inches thick and 8 feet in both width and length.

Artificial hip joints and artificial knee joints must possess high mechanical strength because of the loads these joints will bear over several years. Typically, these joints are constructed of hard metal or ceramic, and are a provided with a relatively softer lining of a UHMWPE at least at the interface of movable part(s). For example, UHMWPE is typically used to construct the lining of an acetabular cup of a prosthetic hip joint.

When used as a load bearing component, UHMWPE typically deteriorates over time due to the continuous wear the component is subjected to. As stated in EP 722 973, "In recent years, it has become increasingly apparent that tissue necrosis and interface osteolysis, in response to UHMW polyethylene wear debris, are primary contributors to the long-term loosening failure of prosthetic joints. For example, the process of wear of acetabular cups of UHMW polyethylene in artificial hip joints introduces many microscopic wear particles into the surrounding tissues. The reaction of the body to these particles includes inflammation and deterioration of the tissues, particularly the bone to which the prosthesis is anchored. Eventually, the prosthesis becomes painfully loose and must be revised. It is generally accepted by orthopaedic surgeons and biomaterials scientists that the reaction of tissue to wear debris is the chief cause of long-term failure of such prostheses." See page 2 lines 12–19 thereof.

The prior art teaches that UHMWPE "can be cross-linked by irradiation with high energy radiation, for example gamma radiation in an inert atmosphere or vacuum. Exposure of UHMWPE to gamma irradiation induces a number of free-radical reactions in the polymer. One of these is cross-linking. The free radicals formed upon irradiation of UHMWPE can also participate in oxidation which reduces the molecular weight of the polymer via chain scission, leading to degradation of physical properties, embrittlement and a significant increase in wear rate. The free radicals are very long-lived (greater than eight years), so that oxidation continues over a very long period of time resulting in as much as a 5-fold increase in the wear rate as a result of oxidation over a period of about 5 years. As such, the wear rate of traditionally irradiated materials is significantly greater than unirradiated materials." U.S. Pat. No. 6,017,975 at col. 1 lines 18–35. "Gamma radiation is preferably used in the irradiation step, however electron beam or x-ray radiation may also be used." '975 patent at col. 3 lines 47–49. EP 722 973 provides that "The crosslinking can be achieved by various methods known in the art, for example, by irradiation crosslinking of the molten polymer; photocross-linking of the molten polymer; and crosslinking of the polymer with a free radical generating chemical." EP 722 973 at page 4 lines 18–21.

However, "The free radicals formed upon irradiation of UHMWPE can also participate in oxidation which reduces the molecular weight of the polymer via chain scission, leading to degradation of physical properties, embrittlement and a significant increase in wear rate. The free radicals are very long-lived (greater than eight years), so that oxidation continues over a very long period of time resulting in as much as a 5-fold increase in the wear rate as a result of oxidation over a period of about 5 years. As such, the wear rate of traditionally irradiated materials is significantly greater than unirradiated materials." U.S. Pat. No. 6,017,975 at col. 1 lines 26–36.

In addition to teaching irradiation to effect cross-linking in order to improve wear resistance, the prior art teaches that prosthetic devices can be sterilized at the completion of the manufacturing process by irradiating the device. See, e.g., the '975 patent at col. 1 lines 37–50. However, "sterilization of polyethylene joint components with gamma irradiation followed by storage on a shelf contributes to oxidative degradation. The degradative changes continue with time and occur not only on the surface but also through the bulk of the component. Alterations in the material properties associated with the degradation increase the stresses on the surface of and within the polyethylene total joint replacement components once these components have been implanted and are subject to loading in vivo. Thus, the wear resistance of a polyethylene component that has been stored on a shelf for an extended time may be diminished before the component is implanted." The Journal of Bone and Joint Surgery, vol. 76-A, no.7, July 1994 pp. 1052–1055 (see page 1052).

SUMMARY OF THE INVENTION

The present invention is a method for forming a shaped article of UHMWPE, such as the components of a prosthetic device, and in particular, the load bearing components thereof. The method comprises the steps of a) forming, under heat and pressure, ultra high molecular weight polyethylene into a shaped article;

b) cooling the shaped article;

c) cross-linking the ultra high molecular weight polyethylene of the shaped article, preferably by irradiating it, more preferably by irradiating it with gamma radiation;

d) heating the shaped article to a temperature below the melting point of the ultra high molecular weight polyethylene; and e) sterilizing the shaped article using non-crosslinking sterilization means, such as exposure to ethylene oxide or gas plasma.

Without wishing to be bound by any theory, it is believed that following the irradiation step with the heating step reduces or minimizes the detrimental affects associated with irradiation. The present applicant offers no view as to why this is the case, or what mechanism causes the improvement. The applicant notes that others have offered a hypothesis for what occurs when an irradiation step is followed by heating "near or above the melting point". See U.S. Pat. No. 6,017,975 at col. 2 lines 26–30. The applicant expresses no view at this time concerning the correctness of this hypothesis.

DETAILED DESCRIPTION OF THE PREFERRED EMBODIMENT

Any of the UHMWPE resins that have been used to form prosthetic devices can be employed in the present inventive method. A non-inclusive list of those resins include GUR 4150, GUR 1150 Premium, and GUR 1050 Premium. The applicants have found that another resin, the GUR 1020 Premium resin, is particularly well suited for the present application due to its very good wear properties. Also when a direct compression molding step is employed, the desired dimensions of the parts are achieved time after time with this resin. These resins are available from Ticona, of League City, Tex.

Any technique known for forming or shaping prosthetic devices from the stock polymeric material can be employed in the present invention, including direct compression molding, the machining of ram extruded bars, or the machining of parts from large molded sheets. A particularly well suited formation technique is a direct compression molding process in which the resin is heated and compressed in a mold at temperatures between 300° F. and 425° F., and pressures between 900 and 1600 psi, for a time period ranging from about 20 and 80 minutes. The resulting shaped article is then cooled to a temperature below 200° F., and separated from the mold. Cooling may be effected gradually, that is, the article can be cooled at a rate less than about 4° C. per minute.

Certain surface details, such as undercuts, can not be formed when direct compression molding is employed. If desired, these surfaces may be formed by a machining operation conducted at this time, or any time later in the process before the sterilization step.

The UHMWPE of the shaped article is then crosslinked using methods known in the art. The applicants have found that irradiating the shaped article with a dose of gamma radiation is well suited for this process, but it may be initiated with other forms of radiation, or by photoinitiating a cross-linking reaction within the polymer, or by initiating a reaction with a cross-linking chemical. Electron beam radiation and x-ray radiation may also be used. During irradiation, the shaped article is placed in a protective container and passed through a gamma radiation source and irradiated with a dose between 4 megarads and 7 megarads.

The irradiated shaped article is then heated in a heat source, such as an oven to a temperature that is below the melting temperature of UHMWPE, which is approximately 285° F. The article is heated for a period of time, which will vary depending on the temperature at which the article is heated. Large periods of time will be required for lower temperatures, such as temperatures of 200° F. Shorter periods of time will be required where the heating temperature approaches the melting point of the material. For example, at temperatures of about 50° C., 48 hours may be required while at 100° C. one to two hours may be sufficient.

The heating may optionally be conducted in an inert gas, which is preferable when heating when place over an extended period, as the inert atmosphere limits the degree of oxidation that occurs on the surface of the part.

After heating, the article is sterilized using a method and apparatus that do not induce free radical formation. Suitable sterilization processes include gas plasma or ethylene oxide. For example a PLAZLYTE® gas plasma sterilization unit, manufactured by Abtox (Mundelein, Ill.), may be used. The shaped article is packaged in a container, which may be an environment free of an oxidation inducing components or it may be air.

By undertaking the process disclosed above, it is believed that a shaped article is produced which is more resistant to abrasive wear, while at the same time maintaining the mechanical properties possessed by the UHMWPE. It is turter believed that the process described herein reduces or minimizes the detrimental effects associated with irradiation.

It will be appreciated by those skilled in the art that the present invention is not limited to the particular embodiments shown and described herein, and that variations may be made which are within the scope of the accompanying claims without departing from the principle of the invention and without sacrificing its chief advantages.

I claim:

1. A method for forming a shaped article of an ultra high molecular weight polyethylene comprised of the steps of:
    a) forming ultra high molecular weight polyethylene into a shaped article;
    b) cooling the shaped article;
    c) cross linking the ultra high molecular weight polyethylene of the shaped article;
    d) heating the shaped article to a temperature below the melting point of the ultra high molecular weight polyethylene; and
    e) sterilizing the shaped article using non-free radical generating sterilization means.

2. The method of claim 1 wherein the shaped article is formed by compression molding.

3. The method of claim 1 wherein the shaped article is formed by ram extrusion and machining.

4. The method of claim 1 wherein the forming of the shaped article is comprised of the steps of:
    a) heating and compressing an ultra high molecular weight polyethylene resin in a mold at temperatures between about 300° F. and 425° F. and pressures between about 900 psi and 1600 psi;
    b) maintaining the pressure and temperature for about 20 to 80 minutes;
    c) cooling the mold and shaped article to a temperature below 200° F.: and
    d) separating the part from the mold.

5. The method of claim 1 wherein the cross linking is effected by irradiation.

6. The method of claim 1 wherein the cross linking is effected by irradiation with a gamma radiation source.

7. The method of claim 1 wherein the cross linking is effected by method comprised of the steps of:
    a) sealing the shaped article in a protective container;
    b) passing the article and the container through a gamma radiation source and irradiating the article with a radiation dose of about 4 to 7 megarads; and
    c) removing the article from the container.

8. The method of claim 1 wherein the heating of the cross-linked shaped article is effected in an oven at temperatures in the range of about 200° F. to about 285° F.

9. The method of claim 8 wherein the heating of the cross-linked shaped article is effected in an inert atmosphere.

10. The method of claim 1 wherein the sterilizing step is comprised of sealing the shaped article in a container and sterilizing the preform using gas plasma or ethylene oxide.

11. The method of claim 1 wherein the shaped article is a prosthetic device or a component thereof.

12. The method of claim 1 wherein the shaped article is a prosthetic device or a load bearing component thereof.

13. The method of claim 1 wherein the shaped article is the acetabular bearing component of hip joint prosthesis.

14. A method for forming a shaped article of an ultra high molecular weight polyethylene comprised of the steps of:
   a) forming, under heat and pressure, ultra high molecular weight polyethylene into a shaped article;
   b) cooling the shaped article;
   c) cross linking the ultra high molecular weight polyethylene of the shaped article;
   d) heating the shaped article to a temperature below the melting point of the ultra high molecular weight polyethylene; and
   e) sterilizing the shaped article without resort to irradiation.

15. The method of claim 14 wherein the shaped article is formed by compression molding and machining.

16. The method of claim 14 wherein the shaped article is formed by ram extrusion and machining.

17. The method of claim 14 wherein the forming of the shaped article is comprised of the steps of:
   a) heating and compressing an ultra high molecular weight polyethylene resin in a mold at temperatures between about 300° F. and 425° F. and pressures between about 900 psi and 1600 psi;
   b) maintaining the pressure and temperature for about 20 to 60 minutes;
   c) cooling the mold and shaped article to a temperature below 200° F.: and
   d) separating the part from the mold.

18. The method of claim 14 wherein the cross linking is effected by irradiation.

19. The method of claim 14 wherein the cross linking is effected by irradiation with a gamma radiation source.

20. The method of claim 14 wherein the cross linking is effected by method comprised of the steps of:
   a) sealing the shaped article in a protective container;
   b) passing the article and the container through a gamma radiation source and irradiating the article with a radiation dose of about 4 to 7 megarads; and
   c) removing the article from the container.

21. The method of claim 14 wherein the heating of the cross-linked shaped article is effected in an oven at temperatures in the range of about 120° F. to about 285° F.

22. The method of claim 21 wherein the heating of the cross-linked shaped article is effected in an inert atmosphere.

23. The method of claim 14 wherein the sterilizing step is comprised of sealing the shaped article in a container and sterilizing the preform using gas plasma or ethylene oxide.

24. The method of claim 14 wherein the shaped article is a prosthetic device or a component thereof.

25. The method of claim 14 wherein the shaped article is a prosthetic device or a load bearing component thereof.

26. The method of claim 14 wherein the shaped article is the acetabular bearing component of hip joint prosthesis.

* * * * *